(12) United States Patent
Hoth et al.

(10) Patent No.: US 7,543,989 B2
(45) Date of Patent: Jun. 9, 2009

(54) LIFTING UNIT

(75) Inventors: Tobias Hoth, Pegnitz (DE); Paul Weidner, Pressath (DE)

(73) Assignee: Siemens Aktiengesellschaft, Munich (DE)

( * ) Notice: Subject to any disclaimer, the term of this patent is extended or adjusted under 35 U.S.C. 154(b) by 86 days.

(21) Appl. No.: 11/542,428

(22) Filed: Oct. 3, 2006

(65) Prior Publication Data

US 2007/0079443 A1 Apr. 12, 2007

(30) Foreign Application Priority Data

Oct. 10, 2005 (DE) .................. 10 2005 048 392

(51) Int. Cl.
*A61B 6/04* (2006.01)
(52) U.S. Cl. .................. 378/209; 378/177; 378/195
(58) Field of Classification Search .................. 378/20, 378/68, 177, 178, 195, 208, 209; 600/410, 600/411, 415, 425, 427; 5/601, 611–613, 5/616, 617; 108/138, 143, 145, 147, 10
See application file for complete search history.

(56) References Cited

U.S. PATENT DOCUMENTS

| 2,884,989 | A | * | 5/1959 | De Fore ..................... 108/138 |
| 3,158,742 | A | * | 11/1964 | Morel et al. ................. 378/209 |
| 3,237,921 | A | * | 3/1966 | Jay ............................ 254/122 |
| 3,334,951 | A | * | 8/1967 | Douglass, Jr. et al. ....... 312/209 |
| 3,793,652 | A | * | 2/1974 | Linehan et al. .............. 5/607 |
| 4,131,801 | A | * | 12/1978 | Hogan ......................... 5/601 |
| 4,374,497 | A | * | 2/1983 | Harmand ..................... 108/4 |
| 4,449,262 | A | * | 5/1984 | Jahsman et al. .............. 5/601 |
| 4,451,945 | A | * | 6/1984 | Heinz et al. .................. 5/601 |
| 4,613,122 | A | * | 9/1986 | Manabe ....................... 5/601 |
| 4,836,520 | A | * | 6/1989 | Span ........................... 5/601 |
| 4,914,682 | A | * | 4/1990 | Blumenthal ................. 378/20 |
| 5,794,541 | A | * | 8/1998 | Hirose ........................ 108/20 |
| 5,862,549 | A | * | 1/1999 | Morton et al. ............... 5/610 |
| 5,953,776 | A | * | 9/1999 | Sanders et al. .............. 5/611 |
| 6,085,670 | A | * | 7/2000 | Genov ........................ 108/147 |
| 6,416,219 | B1 | * | 7/2002 | Pflaum et al. ............... 378/209 |
| 6,637,056 | B1 | * | 10/2003 | Tybinkowski et al. ........ 5/611 |
| 6,640,364 | B1 | * | 11/2003 | Josephson et al. ........... 5/601 |
| 6,675,415 | B2 | * | 1/2004 | Wong .......................... 5/601 |
| 6,986,179 | B2 | * | 1/2006 | Varadharajulu et al. ...... 5/611 |

FOREIGN PATENT DOCUMENTS

DE 11 30 555 C 5/1962
DE 0 357 935 B1 12/1993

OTHER PUBLICATIONS

German Office Action dated Jul. 18, 2006.
English translation of German Patent Office Action dated Jul. 18, 2006 for DE 10 2004 049 392.5-35.

* cited by examiner

*Primary Examiner*—Edward J Glick
*Assistant Examiner*—Thomas R Artman
(74) *Attorney, Agent, or Firm*—Brinks, Hofer, Gilson & Lione

(57) ABSTRACT

A medical lifting device is provided. The medical lifting device comprises a lifting unit that is operable in a linear motion. A spindle drive is operable to adjust the lifting unit. A first ball joint is disposed in the lifting unit and a second ball joint is disposed where the spindle drive is respectively supported.

20 Claims, 4 Drawing Sheets

LIFTING UNIT

The present patent document claims the benefit of the filing date of DE 10 2005 048 392.5, filed Oct. 10, 2005.

BACKGROUND

1. Field

The present embodiments relate to a lifting unit and to a patient support device.

2. Related Art

Medical diagnostics and therapy devices generally include a lifting or telescopic apparatus that adjusts equipment components. Equipment components that are commonly adjusted are, for example, X-ray emitters, X-ray detectors, object tables in mammography, C-arcs, operating tables or patient support apparatuses for C-arcs, computer tomography equipment, magnetic resonance equipment or nuclear medicine and radiation therapy equipment. Radiation, electromagnetic waves or sound waves can be used to examine or treat patients in such devices. For example, X-, electron, or particle rays, ultrasonic waves or magnetic fields can be used for treatment. Generally, the devices include relatively heavy (massive) radiation or active sources and heavy detectors. These devices are positioned in space with corresponding massive mechanical structures. The ability to position this massive mechanical structure in three dimensions is limited by the size of the structure.

Depending on the type of the examination or treatment to be carried out, the diagnostic and/or therapeutic device (termed simply DT device below) and/or its active source are brought into a specific spatial orientation and position with reference to the patient to be examined. The setting of the required spatial configuration requires devices that can be positioned in space. However, because of the generally restricted positioning ability, not every desired spatial configuration of patient and device can be produced. Depending on the type of examination or treatment, it may be necessary to position the patient in a specific way, for example, lying supine or on the side, head over heels or standing. A patient support apparatus has been conventionally used to position the patient with reference to the device. The simultaneous positioning ability of the device and of the patient increases the multiplicity of possible spatial configurations.

A patient support apparatus has one- or two-dimensional displacement in a geodetic, horizontal plane. Patient support tables generally have a patient support (table plate) that is supported in a floating fashion. The patient support may be constructed with or without linear guidance such that the patient support can be adjusted in terms of one dimension or two dimensions. In addition, the patient support can be adjusted in the height direction. Generally, a lifting device that is oriented in a geodetically vertical direction is used to raise or lower the patient support, for example, from below the patient support. The lifting apparatus can include a hydraulic, pneumatic or electric motor drive unit and have a scissor parallelogram mechanism or spindle drive mechanism. The patient support can be tilted or canted. The ability to freely position the patient support, and thus the patient, is achieved by combining all the possibilities of adjustment.

In medical practice, the ability to access the patient with as little hindrance and as freely as possible is of great value. In the course of treatment or examination, medical or technical experts should be able to approach the patient at any time. The patient support apparatus includes a supporting foot that supports the patient, is as slim as possible, and takes up little space. Depending on the patient's position, the centroid of a recumbent patient is not always situated above the supporting foot. The torque on the supporting foot is adversely affected when a patient is not positioned centrally over the supporting foot. If the patient support is displaced horizontally, this torque increases because the lever is longer. Conventionally, the supporting foot design presents a compromise between the smallest possible overall size and high stability.

A lifting apparatus for height adjustment is generally disposed in the supporting foot of the height-adjustable patient support apparatus. The lifting apparatus is subjected to the torque loading described. The torque from a patient who is not centrally recumbent leads, for example, to the vertically oriented lifting apparatus being subject to rotational and shear loads. This loading creates alignment errors in drive components that must be aligned vertically. This can apply, for example, when a hydraulic apparatus having hydraulic cylinders and pistons has a spindle drive with a spindle and nut.

A hydraulic apparatus normally has relatively large lateral guidance forces, and counteracts alignment errors by itself. However, spindle drives are vulnerable to the described problem of alignment errors. For example, a scissor mechanism or double scissor mechanism that is driven by a spindle drive has been used to adjust the height of the patient support. The scissor mechanism or double scissor mechanism is typically connected to a base plate of the patient support apparatus with a fixed bearing. The spindle of the spindle drive forms with a drive motor a structural unit that is permanently connected to the base plate. The spindle is oriented vertically when the structural unit of spindle and drive unit is connected to the base plate. The spindle nut is aligned with the spindle on the scissor mechanism or double scissor mechanism. Conventionally, if a patient who is not recumbent in a centered fashion is loaded on the patient support, the torque causes the scissor mechanism or double scissor mechanism to depart slightly from its originally vertical orientation through elastic deformation. The spindle nut is also deflected out of its position or alignment and is no longer in alignment with the spindle.

Similar problems arise when positioning devices other than patient support tables. For example, a C-arc is generally rotated on two axes, but can be moved vertically and horizontally. The considerable weight of the C-arc and the holder, which is typically on the side of the support, creates torques that deflects the vertical drive and the horizontal drive out of alignment.

The spindle nut has been made of relatively soft material, for example, plastic or bronze to counteract the problem of alignment errors between the spindle and the spindle nut and to provide a certain amount of play between the spindle and the spindle nut. The play between the spindle and the spindle nut allows the spindle drive to be operated reliably despite the occurrence of slight alignment errors. However, this increases both friction and wear between the spindle and the spindle nut.

SUMMARY

In one embodiment, a medical lifting device includes a lifting unit that is operable in a linear motion. A spindle drive is operable to adjust the lifting unit. A first ball joint is disposed in the lifting unit, and a second ball joint is disposed where the spindle drive is respectively supported.

In one embodiment, the spindle drive is supported in a ball joint both on a base plate of the DT device and in the component to be driven. The spindle drive is rotated about the center of rotation of the respective ball joint. For example, in one embodiment, the component driven by the spindle drive is loaded eccentrically with reference to the spindle drive. In this embodiment, a torque is exerted on the spindle drive that varies the alignment of the spindle drive, but the spindle drive follows the deflection by rotating about the respective ball joint and thus maintains the proper alignment between the spindle and the spindle nut. Maintaining the alignment prevents or at least minimizes an increase in wear and friction owing to eccentric loading of the component.

In one embodiment, at least one of the ball joints is aligned with the spindle nut of the spindle drive. For example, the load of the component to be driven, which rests on the spindle, is centrally led via the spindle into the ball joint, which minimizes friction and wear inside the ball joint. The ball joint is optimally mobile and effectively compensates for alignment errors in the spindle drive.

In another embodiment, the DT device includes a double scissor mechanism that drives the component to be driven and is driven by the spindle drive. One scissor mechanism each of the double scissor mechanism is supported on the base plate by one fixed bearing each and one movable bearing. The bearing in a fixed bearing is particularly free from design complication.

In one embodiment, the fixed bearing and the alignment of the spindle define a common plane. This common plane enables the spindle drive and scissors movement to cooperate in a manner that is free from friction.

In one embodiment, the center of rotation of the ball joint lies on an axis running through the fixed bearing of the double scissor mechanism. The eccentric loading of the patient support may lead to a deflection of the double scissor mechanism about the fixed bearing, for example, in the form of a rotation. The common axis of the fixed bearings and the ball joint allows the spindle drive to be deflected about the same axis of rotation. Accordingly, alignment errors in the spindle drive due to eccentric loading of the patient support may be minimized or prevented.

In one embodiment, the spindle drive is driven by a drive unit that is permanently connected to the spindle nut, and the spindle nut is rotated. For example, the variation in the connection between spindle nut and drive unit during a rotation of the spindle about the ball joint is prevented. A variable transmission of the driving force of the drive unit to the spindle nut is not needed. Conventionally, a variable transmission was necessary between a fixed drive unit and a spindle nut supported movably with reference to the drive unit in the case of a deflection of the spindle nut. For example, in the conventional embodiment, the distance or spindle nut's orientation relative to the drive unit would be varied in this case.

In another embodiment, the drive unit is elastically supported on the base plate together with the spindle, for example on rubber buffers. The elastic bearing supports the weight of the drive unit, for example, when the drive mass is not arranged with rotational symmetry about the center of rotation of the ball joint. Conventionally, the mass of an eccentric arrangement of the drive unit exerts a torque on the spindle. The elastic bearing of the drive unit prevents the exertion of the torque on the spindle. In one exemplary embodiment, the elastic bearings are suitably moved to enable a (slight) rotation about the ball joint, and thus the spindle movements that maintain the spindle alignment remain possible. The suppression of a torque exerted on the spindle by the drive unit acts to reduce wear and friction in the spindle drive.

In one embodiment, the movably supported drive unit has a nose that engages in an anti-rotation member that is permanently connected to the base plate. The drive unit is secured against rotation because the drive unit must effect a rotation of the spindle. A nose engaging in an anti-rotation member is an anti-rotation member that is particularly free from design complication.

The embodiments described above can be implemented with particular advantage in a patient support apparatus.

DETAILED DESCRIPTION

Figure 1:
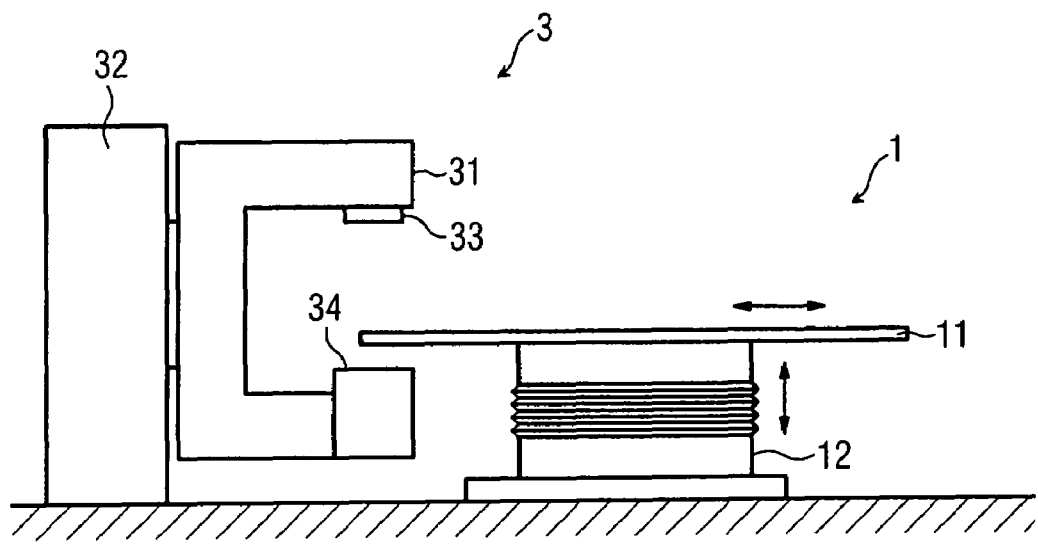
FIG. 1 illustrates a diagnostic and/or therapeutic device having a patient support apparatus.

In one embodiment, as shown in FIG. 1, a diagnostic and/or therapeutic device (DT device) 3 includes a patient support apparatus 1 and a C-arc 31 that carries an X-ray emitter 33 and an X-ray detector 34. For example, the C-arc can be used to generate X-ray images having X-radiation with low energies or therapeutic irradiation having X-radiation with high energies. The C-arc 31 is supported by a C-arc pedestal 32. The C-arc pedestal 32, as shown in FIG. 1, is a structure that is supported by the floor of a room. In alternate embodiments, the C-arc pedestal 32 is supported by the wall or ceiling of the room. The C-arc 31, which positions the X-ray emitter 33 and the X-ray detector 34, and the patient support apparatus 1 are positioned so that a patient is detected by the X-ray beam. In one exemplary embodiment, the C-arc 31 is rotated about at least one horizontal axis (not illustrated) and is moved (not illustrated) vertically in the C-arc pedestal 32.

The patient support apparatus 1 includes a patient support 11. The patient support 11 supports a patient. In one embodiment, the patient support 11 is displaced in a horizontal direction. For example, the horizontal direction is indicated by a horizontally oriented double arrow in FIG. 1. The patient support 11 is supported by a supporting foot 12. For example, the patient support 11 is coupled to the supporting foot 12 in a floating fashion. The height of the patient support 11 is adjustable. The supporting foot 12 includes a lifting apparatus (not illustrated in FIG. 1) to adjust the height of the patient support 11. For example, the height adjustability is indicated by a vertically oriented double arrow in FIG. 1.

Figure 2:
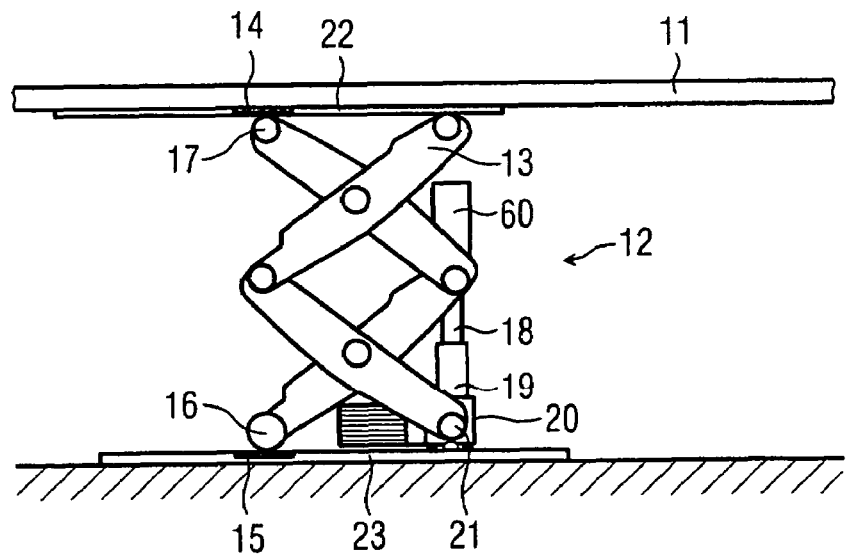
FIG. 2 illustrates a patient support apparatus with lifting scissors and a spindle drive.

In one embodiment, as shown in FIG. 2, the patient support apparatus 1 includes a double scissor mechanism as a lifting apparatus. In one exemplary embodiment, the lifting apparatus includes a base plate 23 that is disposed in the region of the supporting foot 12 and supports the double scissor mechanism 13. The double scissor mechanism 13 is composed of two individual scissor mechanisms arranged next to one another. The double scissor mechanism 13 is operable in the vertical direction. For example, the double scissor mechanism 13 is shortened or lengthened by actuation in a vertical direction. For example, the height of a lifting plate 22, which is supported on a side of one of the two scissor mechanisms, is adjusted by shortening or lengthening the double scissor mechanism 13. The patient support 11 is connected to the lifting plate 22, so that the double scissor mechanism 13 is operable to adjust the height of the patient support 11.

The double scissor mechanism 13 is supported by a fixed bearing 21 on the base plate 23. The fixed bearing 21 is on the opposite side of the base plate 23 as a movable bearing 16, which includes a plane bearing 15. The fixed bearing 21 and movable bearing 16 are operable to actuate the double scissor mechanism 13. The lifting plate 22 is supported on the double scissor mechanism 13 via a movable bearing 17 that includes a plane bearing 14 on the lifting plate 22. On the opposite side of the movable bearing 17, for example, above the fixed bearing 21, the double scissor mechanism 13 is coupled to the lifting plate 22 by a second fixed bearing (not illustrated).

In one embodiment, a spindle drive is coupled to and operable to actuate the double scissor mechanism 13. In alternate embodiments, the spindle drive is, for example, constructed as a trapeze spindle or a recirculating ball spindle. The spindle drive includes a spindle 18 connected to the double scissor mechanism 13 and a spindle nut 19. The spindle 18 is moved axially in the spindle nut 19 by rotating the spindle nut 19 about the spindle 18. The spindle 18 is driven thereby. The spindle 18 is immersed in the tube 60 and is connected to the tube 60 at the end situated on top in the illustration. The movement of the spindle 18 is transmitted to the tube 60. The tube 60 is permanently connected to the double scissor mechanism 13. The tube 60 is operable to drive the double scissor mechanism 13. The height of the double scissor mechanism 13 is adjusted by the axial movement of the spindle 18 and the tube 60.

The rotation of the spindle nut 19 is performed by a drive unit 20 that is connected to the spindle nut 19. The drive unit 20 is operable to drive the spindle nut 20 in a rotating fashion. The drive unit 20 is, but is not limited to, an electric motor. In alternate embodiments, the drive unit 20 is actuated hydraulically, pneumatically, manually or by foot power.

In one embodiment, a torque is exerted on the double scissor mechanism 13. The torque is produced by an eccentric loading of the patient support 11. This torque can effect an elastic deflection that acts, in turn, on the spindle 18. The drive unit 20 is supported by the base plate 23 in a ball joint. The spindle 18 is supported by a ball joint in the tube 60. For example, by rotating about the two ball joints, the spindle 18 and spindle nut 19 can compensate for the eccentric loading and maintain the spindle alignment.

Figure 3:
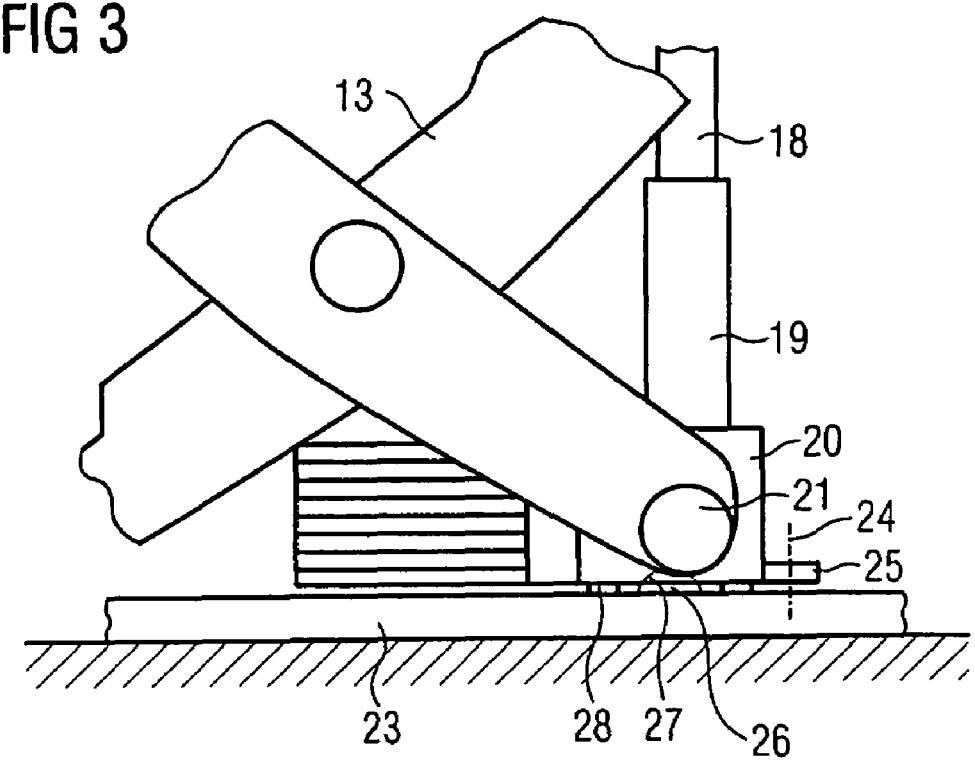
FIG. 3 illustrates a ball joint bearing of a spindle drive.

In one embodiment, as shown in FIG. 3, drive unit 20 includes a ball joint bearing. The spindle nut 19 is permanently connected to the drive unit 20. The drive unit 20 is operable to drive the spindle nut 19 in a rotating fashion. The drive unit 20 and the spindle nut 19 are supported by the base plate 23 via a ball joint. The base plate 23 includes a ball head 26 that covers an approximately 90° section of arcuate angle in the embodiment illustrated. The drive unit 20 and spindle nut 19 are supported on the ball head 26 by a ball socket 27. Any suitable material may be used to make the ball head 26 and ball socket 27. In alternate embodiments, the ball head 26 and ball socket 27 can be hardened or have bearing shells (not shown) or sliding surfaces (not shown) that act to reduce friction and wear.

In one embodiment, the drive unit 20 is arranged with reference to the axis or rotation of the spindle nut 19. The drive unit 20 is arranged with reference to the ball joint and accordingly effects a torque on the spindle drive because of its weight, specifically counterclockwise in the figure. In order to counteract this torque, the drive unit 20 is supported on sprung or elastic elements, specifically on rubber buffers 28. In an alternate embodiment, the drive unit 20 is supported on other suitable elastic bearing elements, for example, steel spring elements. The rubber buffers 28 allow slight movements of the drive unit 20 about the ball joint. The drive unit 20 is self-supporting and exerts no torque on the spindle drive because of the rubber buffers 28. For example, the rubber buffers 28 are dimensioned in such a way that the drive unit 20 remains in the desired position, for example, as illustrated in FIG. 3. In one embodiment, the rubber buffers 28 are not arranged symmetrically about the ball joint, but in a way that the eccentric part of the mass of the drive unit 20 is suitably supported.

In one embodiment, the movable bearing of the drive unit 20 is restricted to the extent that the drive unit 20 must be able to exert a rotating force on the spindle nut 19. For example, the spindle nut 19 is secured against rotation despite the movable bearing. A nose 25 is permanently attached to the drive unit 20 and is operable with an anti-rotation member 24 permanently connected to the base plate 23. Although the drive unit 20 is secured against rotation about the spindle nut 19, the anti-rotation member 24 can follow a rotation about the ball joint as a consequence of an eccentric loading of the patient support 11 and a variation in the alignment of the spindle drive. The bearing of drive unit 20 and spindle nut 19 therefore ensures that alignment errors between spindle nut 19 and spindle 18, which are created by eccentric patient support 11 loading, can be compensated for.

Figure 4:
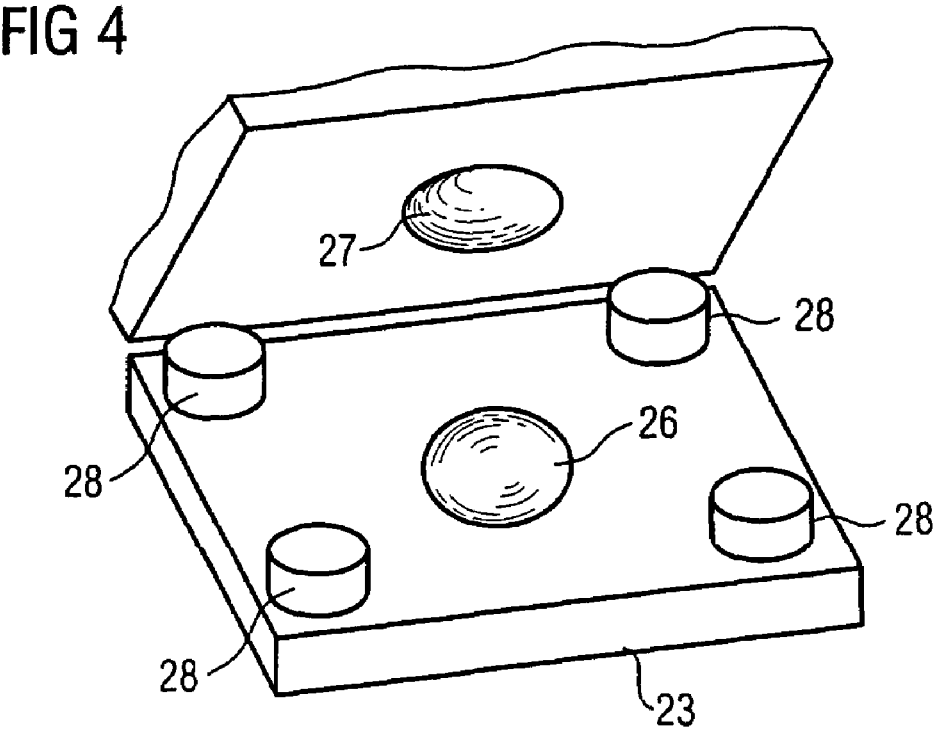
FIG. 4 illustrates a perspective schematic of the ball joint.

In one embodiment, as shown in FIG. 4, a base plate 23 on which the rubber buffers 28 are arranged includes the ball head 26. The ball socket 27 is arranged on the underside of the structural unit of drive unit 20 and spindle nut 19. The section of arcuate angle formed by the ball socket 27 varies depending on design. For example, the ball head 26 can be more or less widely surrounded by the ball socket 27 when the ball joint is assembled. In alternate embodiments, special bearing shells or treated raceways (not shown) of the ball joint are included in the ball joint. In one embodiment, the ball joint is filled with a lubricant (not shown) to reduce friction and/or wear.

Figure 5:
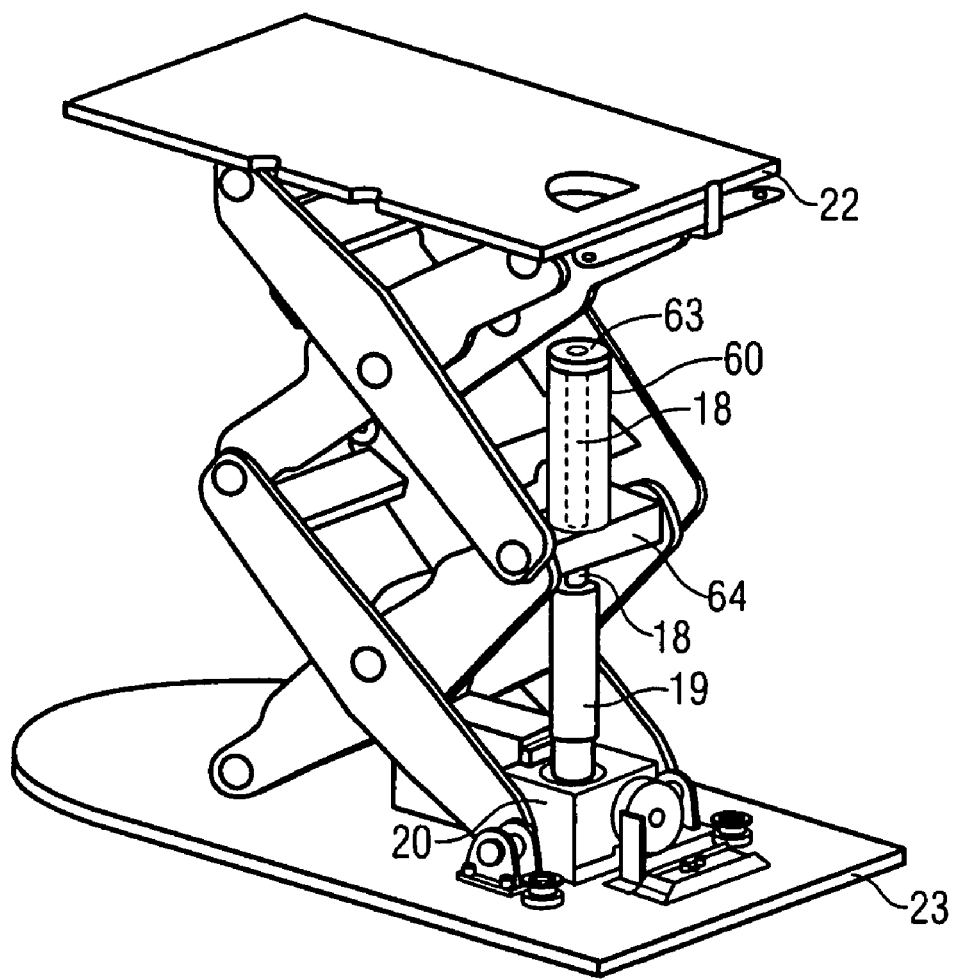
FIG. 5 illustrates a lifting double scissor mechanism with a spindle drive.

In one embodiment, as shown in FIG. 5, a lifting unit includes a double scissor mechanism and a spindle drive. In one embodiment, the lifting unit is operable to adjust the height of a patient support apparatus. However, the lifting unit is not limited to use with patient support apparatuses, for example, in alternate embodiments, the lifting unit is operable to adjust the height of a C-arc unit, a radiation source, a DT device or some other suitable device. In this embodiment, the lifting unit includes a base plate 23 situated at the bottom and on which both the double scissor mechanism and the spindle drive are supported. The height of a lifting plate 22 can be adjusted linearly with reference to the base plate 23 using a double scissor mechanism and spindle drive. The spindle drive includes a drive unit 20 that drives the spindle nut 19. The spindle nut 19 runs about the spindle 18 such that a recirculating ball spindle is formed, which causes the non-rotating spindle 18 to move axially, for example, in the upward or downward direction.

The end of spindle 18 that is opposite the spindle nut 19 is operable in a tube 60. The tube 60 is sealed on the upper side by a tube cap 63. The spindle 18 is connected to the tube cap 63. The tube 60 bears via the tube cap 63 on the upper end of the spindle 18 and is moved upward or downward by the movement of the spindle 18.

In one embodiment, the tube 60 is permanently connected to the cross member 64 of the double scissor mechanism. For example, if the tube 60 is moved upward or downward, the cross member 64 is moved upward or downward. The cross member 64, which is part of the double scissor mechanism forms an axis of the scissor mechanism structure. The upward or downward movement of the cross member 64 shortens or lengthens the double scissor mechanism, which, for example, adjusts the height of the lifting plate 22.

In one embodiment, the inside diameter of the tube 60 is greater than the outside diameter of the spindle nut 19. For example, the tube 60 can slide over the spindle nut 19 or the spindle nut 19 can be immersed in the tube 60. Accordingly, the lifting plate 22 can be lowered as far as possible.

Figure 6:
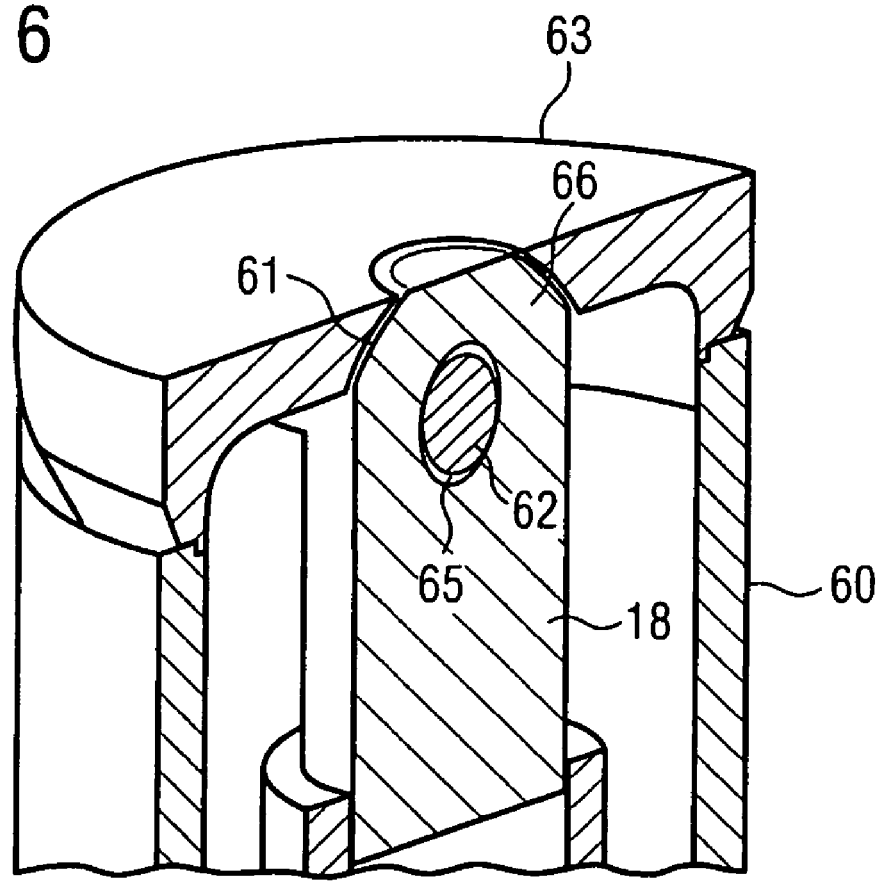
FIG. 6 illustrates the two ball joint bearings of a spindle drive.
Figure 6:
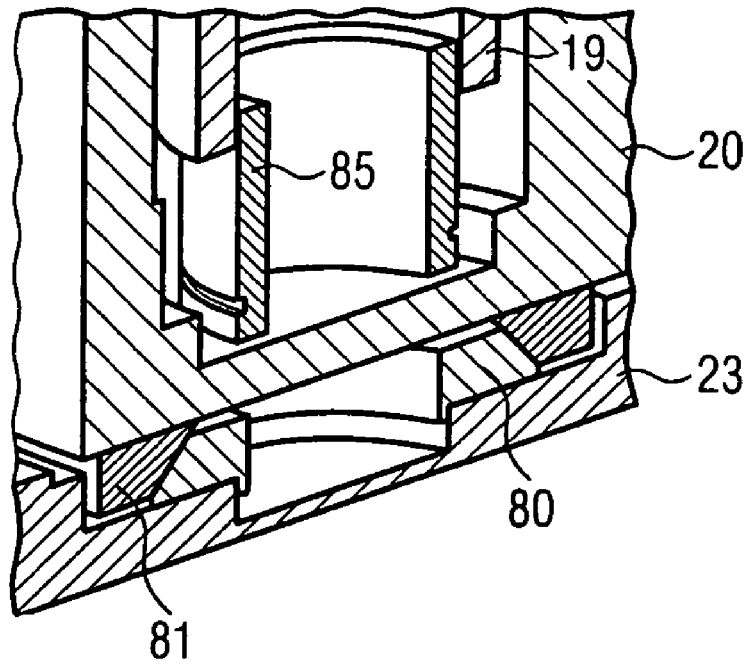

In one embodiment, as shown in FIG. 6, the spindle drive 18 has a respective ball joint bearing at the two ends. The spindle drive includes a tube 60. The drive unit 20 of the spindle drive is supported by a base plate 23. The base plate 23 includes a washer 80 that implements the ball joint bearing. In one embodiment, the washer 80 is spherical. The washer 80 has an outer cheek in the shape of a spherical section that enables easy movement of the ball joint.

The underside of the drive unit 20 has a ball socket washer 81. The ball socket washer 81 has an inner cheek in the shape of a spherical section, which enables easy movement of the ball joint. The respective cheeks, in the shape of a spherical section, of the ball socket washer 81 and of the spherical washer 80 jointly form a ball joint bearing. For example, the arc radii of the ball socket washer 81 and of the spherical washer 80 correspond to each other.

In an alternate embodiment, the inner cheeks of the ball socket washer 81 are constructed as a 90-degree depression, for example, a straight wall. In this alternate embodiment, the ball joint bearing is in cooperation with the spherical washer 80 as a spherical section.

In one embodiment, the drive unit 20 has an axle 85 on which the spindle nut 19 is rotatably supported. The spindle nut 19 is connected to, for example, a motor (not shown). The spindle nut 19 is prevented from making an axial movement.

In one embodiment, the spindle 18 is guided by the spindle nut 19. The spindle nut 19 is formed around the spindle 18. The upper end of the spindle 18 forms a ball head end 66. The outer cheeks of the ball head end 66 are designed in the shape of a spherical section in a way comparable to the outer cheeks of the spherical washer 80. The abutment is formed by the tube cap 63, whose inner cheeks are likewise designed in the shape of a spherical section and form a ball socket ring 61. The spherical radii of the cheeks of the ball socket ring 61 correspond and couple to the ball head end 66. The combination of the ball socket ring 61 and the ball head end 66 forms a ball joint bearing.

In an alternate embodiment, the inner cheeks of the submersible tube cap 63 and of the ball socket ring 61 are formed as a 90-degree depression, for example, a straight wall. In this alternate embodiment, a ball joint bearing is in cooperation with a spherical shape of the ball head end 66 of the spindle 18 as a spherical section.

In one embodiment, the spindle 18 cannot be driven by the spindle nut 19 and rotate about its own axis because it is connected to the tube 60 by a bolt 62. The spindle 18 has a bolt eye 65 through which the bolt 62 is guided. The bolt 62 is connected to the tube 60 so that no rotation is possible about the spindle axis. For example, the tube 60 is connected to the component of the DT device that is to be moved, which makes the tube 60 incapable of rotating.

The present embodiments relate to a diagnostic and/or therapeutic device (DT device). In one embodiment, the DT device includes a component that is supported in a linearly adjustable fashion, and a spindle drive that is designed to adjust the component linearly. Provided in the component and in the remainder of the DT device is one bearing each in which the spindle drive is respectively supported in order to be able to adjust the component linearly relative to the remainder of the DT device. Both bearings are constructed as ball joints. Ball joints enable twisting of the axis of the spindle drive if, for example, the component to be driven should exert a torque on the spindle drive. Alignment errors between spindle nut and spindle can be suppressed together with attendant wear by twisting of the axis of the spindle drive. A particularly advantageous construction results when use is made of the spindle drive in a patient support apparatus having a double scissor mechanism lifting unit.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A medical lifting device comprising:
   a lifting unit that is operable in a linear motion,
   a spindle drive that is operable to adjust the lifting unit, and
   a first ball joint bearing disposed in the lifting unit and a second ball joint bearing that directly contacts the spindle drive, such that the spindle drive is rotationally supported on the second ball joint bearing.

2. The medical lifting device as claimed in claim 1, wherein at least one of the first or second ball joints is axially aligned with a spindle nut of the spindle drive.

3. The medical lifting device as claimed in claim 2, wherein a drive unit is operable to drive the spindle drive and wherein the drive unit is permanently connected with and operative to rotate the spindle nut.

4. The medical lifting device as claimed in claim 3, further comprising a base plate, wherein the drive unit and the spindle drive are supported on the base plate, and wherein the drive unit is supported on the base plate by rubber buffers.

5. The medical lifting device as claimed in claim 4, wherein the drive unit has a nose that is operable with an anti-rotation member that is permanently connected to the base plate.

6. The medical lifting device as claimed in claim 3, wherein the drive unit is elastically supported on the base plate.

7. The medical lifting device as claimed in claim 2, wherein the spindle nut is rotationally operative to axially move a spindle in the spindle nut, wherein one end of the spindle is supported in a tube having a cap at one end of the tube, and wherein the end of the spindle that is supported in the tube being constructed as a ball head end that is supported in a ball socket ring.

8. The medical lifting device as claimed in claim 7, wherein the end of the spindle being supported in the tube has a bolt eye which runs transverse to the axis of the spindle and through which a bolt is guided, the bolt being connected to the tube in such a way as to prevent rotation of the spindle about the spindle axis relative to the tube.

9. The medical lifting device as claimed in claim 7, wherein the spindle nut is operative around the spindle.

10. The medical lifting device as claimed in claim 1, wherein the lifting unit is a double scissor mechanism, wherein the spindle drive is operative to drive the double scissor mechanism, and wherein at least one side of the double scissor mechanism is supported by one fixed bearing and one movable bearing.

11. The medical lifting device as claimed in claim 10, wherein the fixed bearing and the moveable bearing are arranged in such a way that an axis of rotation of the spindle drive is aligned with the fixed bearing of the double scissor mechanism.

12. The medical lifting device as claimed in claim 11, wherein the center of rotation of the first ball joint lies on an axis running through the fixed bearing.

13. The medical lifting device as claimed in claim 1, comprising a patient support that is adjustable in a vertical direction, wherein the spindle drive is operable to adjust the height of the patient support.

14. The medical lifting device as claimed in claim 1, wherein the lifting unit is a double scissor mechanism that is directly connected to a patient support that is operable to support a patient during a medical examination.

15. A diagnostic or therapeutic device comprising:
a patient support apparatus, a diagnostic or therapeutic device, a medical lifting device that is coupled with and operative to adjust the height of the patient support apparatus,
wherein the medical lifting device includes:
a lifting unit that is operable in a linear direction,
a spindle drive that is operable to adjust the lifting unit, the spindle drive having a first ball joint bearing disposed at one end of the spindle drive and a second ball joint bearing disposed at a second end of the spindle drive, where the spindle drive is supported.

16. The diagnostic or therapeutic device as claimed in claim 15, wherein the diagnostic or therapeutic device is a C-arc that includes an X-ray emitter and a X-ray detector.

17. The diagnostic or therapeutic device as claimed in claim 15, wherein the diagnostic or therapeutic device is adjustable in a direction parallel to the linear direction of the lifting unit.

18. The diagnostic or therapeutic device as claimed in claim 17, wherein the height adjustment of the lifting unit corresponds to the height adjustment of the diagnostic or therapeutic device.

19. The diagnostic or therapeutic device as claimed in claim 15, wherein the lifting unit is a double scissor mechanism.

20. The diagnostic or therapeutic device as claimed in claim 15, further comprising: a ball socket washer that aligns the second ball joint bearing, which supports the spindle drive, with the spindle drive and that allows the second ball joint bearing to move.

* * * * *